United States Patent [19]

Payne et al.

[11] Patent Number: 5,348,547
[45] Date of Patent: Sep. 20, 1994

[54] ABSORBENT MEMBERS HAVING IMPROVED FLUID DISTRIBUTION VIA LOW DENSITY AND BASIS WEIGHT ACQUISITION ZONES

[75] Inventors: Michael Payne, Forest Park; Robert W. Perkins, Hamilton; Danny R. Moore, West Chester, all of Ohio

[73] Assignee: The Procter & Gamble Company, Cincinnati, Ohio

[21] Appl. No.: 42,950

[22] Filed: Apr. 5, 1993

[51] Int. Cl.$^5$ .............................................. A61F 13/15
[52] U.S. Cl. .................................... 604/378; 604/379; 604/383
[58] Field of Search ................. 604/358, 383, 378, 379

[56] References Cited

U.S. PATENT DOCUMENTS

| | | | |
|---|---|---|---|
| Re. 32,649 | 4/1988 | Brandt et al. | 604/368 |
| 3,224,926 | 12/1965 | Bernardin | 162/146 |
| 3,241,553 | 3/1966 | Steiger | 128/156 |
| 3,440,135 | 4/1969 | Chung | 162/157 |
| 3,658,613 | 4/1972 | Steiger | 156/153 |
| 3,848,594 | 11/1974 | Buell | 128/284 |
| 3,860,003 | 1/1975 | Buell | 128/287 |
| 3,932,209 | 1/1976 | Chatterjee | 162/157 C |
| 4,027,672 | 6/1977 | Karami | 128/284 |
| 4,035,147 | 7/1977 | Sangenis et al. | 8/116.4 |
| 4,076,663 | 2/1978 | Masuda et al. | 260/17.4 GC |
| 4,081,301 | 3/1978 | Buell | 156/164 |
| 4,184,498 | 1/1980 | Franco | 128/290 R |
| 4,213,459 | 7/1980 | Sigl et al. | 128/287 |
| 4,449,979 | 5/1984 | Holtman | 604/379 |
| 4,496,358 | 1/1985 | Karami et al. | 604/378 |
| 4,515,595 | 5/1985 | Kievit et al. | 604/385 A |
| 4,573,986 | 3/1986 | Minetola et al. | 604/366 |
| 4,610,678 | 9/1986 | Weisman et al. | 604/368 |
| 4,643,726 | 2/1987 | Gegelys | 604/368 |
| 4,654,039 | 3/1987 | Brandt et al. | 604/368 |
| 4,673,402 | 6/1987 | Weisman et al. | 604/368 |
| 4,685,915 | 8/1987 | Hasse et al. | 604/378 |
| 4,820,295 | 4/1989 | Chapas et al. | 604/385.1 |
| 4,822,453 | 4/1989 | Dean et al. | 162/157.6 |
| 4,834,735 | 5/1989 | Alemany et al. | 604/368 |
| 4,888,093 | 12/1989 | Dean et al. | 162/157.6 |
| 4,898,642 | 2/1990 | Moore et al. | 162/157.6 |
| 4,935,022 | 6/1990 | Lash et al. | 604/368 |
| 4,988,344 | 6/1991 | Reising et al. | 604/368 |
| 4,988,345 | 1/1991 | Reising | 604/368 |
| 5,009,650 | 4/1991 | Bernardin | 604/378 |
| 5,047,023 | 9/1991 | Berg | 604/368 |
| 5,137,537 | 8/1992 | Herron et al. | 8/120 |
| 5,149,334 | 9/1992 | Lahrman et al. | 604/367 |
| 5,151,092 | 9/1992 | Buell et al. | 604/385.2 |
| 5,176,668 | 1/1993 | Bernardin | 604/368 |

FOREIGN PATENT DOCUMENTS

| | | |
|---|---|---|
| 251676 | 1/1988 | European Pat. Off. . |
| 252650 | 1/1988 | European Pat. Off. . |
| 391814 | 10/1990 | European Pat. Off. ..... D01D 5/253 |
| WO91/11162 | 8/1991 | PCT Int'l Appl. .......... A61F 13/15 |
| WO91/11163 | 8/1991 | PCT Int'l Appl. .......... A61F 13/15 |
| WO91/11165 | 8/1991 | PCT Int'l Appl. .......... A61F 13/52 |
| WO91/11978 | 8/1991 | PCT Int'l Appl. .......... A61F 13/46 |

*Primary Examiner*—Randall L. Green
*Assistant Examiner*—Rob Clarke
*Attorney, Agent, or Firm*—William Scott Andes; E. Kelly Linman

[57] ABSTRACT

An absorbent article having a dual-layer absorbent member, wherein the deposition region of its upper acquisition layer comprises a distribution zone and an acquisition zone having a lower average density and a lower average basis weight per unit area than the distribution zone. The acquisition zone is positioned toward the front of either the absorbent member or the absorbent article so that the acquisition zone may most effectively and efficiently rapidly acquire discharged liquids. The lower storage layer comprises a mixture of hydrophilic fibrous material and discrete particles of absorbent gelling material having a particular size distribution so as to enhance the absorbent capacity and acquisition rate of the dual-layer absorbent member. The upper acquisition layer comprises a homogeneous composition of stiffened, twisted, and curled cellulose fibers which provide enhanced wicking action in the densified distribution zone. The upper acquisition layer serves to rapidly and evenly distribute fluids to the lower storage layer for storage, while freeing the acquisition zone for the next discharge of fluid.

20 Claims, 2 Drawing Sheets

ABSORBENT MEMBERS HAVING IMPROVED FLUID DISTRIBUTION VIA LOW DENSITY AND BASIS WEIGHT ACQUISITION ZONES

FIELD OF THE INVENTION

This invention relates to absorbent members (fibrous web structures) having an acquisition layer comprising a homogeneous composition of hydrophilic fibrous material and a storage layer comprising a mixture of hydrophilic fibrous material and discrete particles of absorbent gelling material. More particularly, the invention relates to a dual-layer absorbent member having an acquisition layer with a relatively lower average density and lower average basis weight acquisition zone positioned in the area of typical liquid deposition to more quickly acquire and distribute liquids within the absorbent member.

BACKGROUND OF THE INVENTION

Absorbent articles such as disposable diapers, adult incontinent pads, sanitary napkins and the like are generally provided with absorbent members, fibrous web structures which comprise entangled masses of fibers, to receive and retain bodily fluids. In order for such absorbent articles to function efficiently, the absorbent members must quickly acquire bodily fluids into the structure from the point of application and subsequently distribute the fluids within and throughout the absorbent member to provide maximum liquid containment. In addition, the absorbent members should be capable of retaining liquids when placed under loads. Prior art attempts to improve the effectiveness of such absorbent members have included distributing particles of absorbent gelling material throughout or in portions of the absorbent member. For example, U.S. Pat. No. 4,610,678, entitled "High-Density absorbent Structures" which issued to Paul T. Weisman and Stephen A. Goldman on Sep. 9, 1986, discloses absorbent members wherein particles of absorbent gelling material (hydrogel) are dispersed in an air-laid web of hydrophilic fibrous material and compressed to a particular density. In addition, U.S. Pat. No. 4,673,402, entitled "Absorbent Articles With Dual-Layered Cores" which issued to Paul T. Weisman, Dawn I. Houghton and Dale A. Gelleft on Jun. 16, 1987, discloses a dual-layer absorbent core wherein an absorbent acquisition layer overlays a lower fluid storage layer that consists essentially of a uniform combination of hydrophilic fibrous material and discrete particles of absorbent gelling material. These patents are incorporated herein by reference.

Other references which disclose dual-layer absorbent members in combination with absorbent gelling materials are PCT Published Applications WO 91/11162, WO 91/11163, and WO 91/11165, each having been published on Aug. 8, 1991. These published patent applications were each filed in the name of the Procter & Gamble Company, and each is hereby incorporated herein by reference.

U.S. Pat. No. 5,047,023, entitled "Absorbent Members Having Low Density and Basis Weight Acquisition Zones", which issued to Charles J. Berg on Sep. 10, 1991, and U.S. Pat. No. 4,834,735, entitled "High Density Absorbent Members Having Lower Density and Basis Weight Acquisition Zones", which issued to Miguel Alemany and Charles J. Berg on May 30, 1989, disclose absorbent articles incorporating such absorbent gelling materials into absorbent members which have selective densification. These patents are also incorporated herein by reference.

Absorbent gelling materials are polymeric materials which are capable of absorbing large quantities of liquids such as water and body wastes relative to their weight, and which are further capable of retaining such absorbed liquids under moderate pressures. These absorption characteristics of absorbent gelling materials make them especially useful for incorporation into absorbent articles such as disposable diapers, adult incontinent pads, sanitary napkins and the like. However, in spite of the extremely high absorption capacities of such absorbent gelling materials, their performance when used in disposable absorbent articles has still not been optimized.

The effectiveness of absorbent gelling materials in disposable absorbent articles is quite dependent upon the form, position, size, and/or manner in which the particles of absorbent gelling material are incorporated into the absorbent member. One way to theoretically improve the absorbent capacity of an absorbent article would be to increase the level of absorbent gelling material in the absorbent member. Unfortunately, however, the effectiveness of absorbent members containing higher concentrations of particles of absorbent gelling material can be adversely affected by a phenomenon called gel blocking. The term "gel blocking" describes a situation that occurs when a particle of absorbent gelling material is wetted. the surface of the particles swelling so as to inhibit liquid transmission into the interior of the absorbent member. Wetting of the interior of the absorbent member, therefore, takes place via a very slow diffusion process. In practical terms, this means that acquisition of liquids by the absorbent member is much slower than the discharge of the liquid to be absorbed, and leakage from the absorbent article may take place well before the particles of absorbent gelling material in the absorbent member are fully saturated or before the liquid can diffuse or wick past the "blocking" particles into the rest of the absorbent member. Often, the storage capacities of areas of the absorbent member remote from the liquid deposition go un-utilized.

Another reason why many absorbent articles are subject to leakage is inability to absorb second and subsequent discharges of fluid even if the first discharge has been effectively absorbed. After a discharge of fluid occurs, the fluid tends to remain situated in the region proximate to the discharge. This is due to the inability of the absorbent core to transport discharged fluid away from the region of discharge once the absorbent capacity of that region has reached the saturation point.

In absorbent members incorporating comparatively higher concentrations of absorbent gelling materials in the interest of higher storage capacity, the problem is aggravated by the fact that in order to increase the amount of absorbent gelling material while maintaining a constant thickness, less hydrophilic fibrous material can be included in the storage layer. The role of the fibrous material in providing wicking capability within the absorbent gelling material-containing storage layer and maintaining a fiber/absorbent gelling material matrix is greatly reduced, necessitating some other method of acquiring and distributing fluid within the absorbent member to regions of the storage layer remote from the liquid infusion.

Thus, it would be advantageous to provide a multi-layer absorbent member that more quickly acquires and distributes liquids within itself while minimizing gel blocking in the storage layer during the liquid acquisition phase. It is therefore a primary objective of the present invention to provide improved absorbent members which are especially effective and efficient in their use of absorbent gelling materials.

It is a further object of the present invention to provide absorbent members of improved capacity and efficiency by utilizinq an acquisition layer of selectively densified, hydrophilic fibrous material to effectively acquire and distribute fluid to a storage layer which includes a comparatively higher concentration of absorbent gelling material.

SUMMARY OF THE INVENTION

The present invention provides absorbent articles such as disposable diapers, incontinent pads, sanitary napkins or the like that have absorbent members that are suitable for acquiring and containing liquids in an especially effective and efficient manner. Such absorbent articles typically comprise a liquid pervious topsheet, a usually liquid impervious backsheet, and an absorbent member positioned between the topsheet and the backsheet.

The present invention relates to dual-layer absorbent members of the type having an absorbent acquisition layer comprising a homogeneous composition of hydrophilic fibrous material in fluid communication with a storage layer comprising a mixture of hydrophilic fibrous material and discrete particles of absorbent gelling material having particular particle size distributions. The acquisition layer has a top surface area which is from about 0.70 to about 1.0 times the top surface area of the storage layer. The absorbent member is typically positioned relative to the backsheet of the absorbent article such that at least about 75% of the absorbent gelling material is found within the front two-thirds portion of the absorbent article. The acquisition zone of the acquisition layer is also typically positioned relative to the backsheet such that it is completely positioned within the front two-thirds portion of the absorbent article.

The acquisition layer has a distribution zone of a relatively high density and high basis weight to distribute and disperse liquids acquired by the acquisition layer to the underlying storage layer and an acquisition zone of a relatively lower average density and lower average basis weight than the distribution zone to quickly acquire and temporarily hold discharged liquids. The acquisition zone then quickly distributes fluid to the storage layer and to the adjoining distribution zone so as to be free to acquire a subsequent discharge of fluid.

In accordance with one aspect of the present invention, the acquisition zone is positioned toward the front of the absorbent member so that the acquisition zone may be positioned in the area of typical liquid deposition. The acquisition zone is also sized so that the top surface area of the acquisition zone comprises less than about 50% of the top surface area of the acquisition layer of the absorbent member.

In accordance with another aspect of the present invention, particles of absorbent gelling material havng a particle size distribution such that the particles have a mass median particle size greater than or equal to about 400 microns is mixed with hydrophilic fibrous material to minimize gel blocking and/or to help maintain an open capillary structure within the storage layer to enhance planar transport of liquids away from the area of typical liquid deposition to the rest of the absorbent member. In addition, the particle size distribution of the absorbent gelling material is controlled to improve absorbent capacity and efficiency of the particles employed in the absorbent member. The mixture of hydrophilic fibrous material and relatively large particles of absorbent gelling material in combination with an acquisition layer with a relatively low density and basis weight acquisition zone provides an improved absorbent member.

DETAILED DESCRIPTION OF THE DRAWINGS

While the specification concludes with claims which particularly point out and distinctly claim the subject matter regarded as forming the present invention, it is believed the invention will be better understood from the following description taken in conjunction with the accompanying drawings in which:

DETAILED DESCRIPTION OF THE INVENTION

Figure 1:
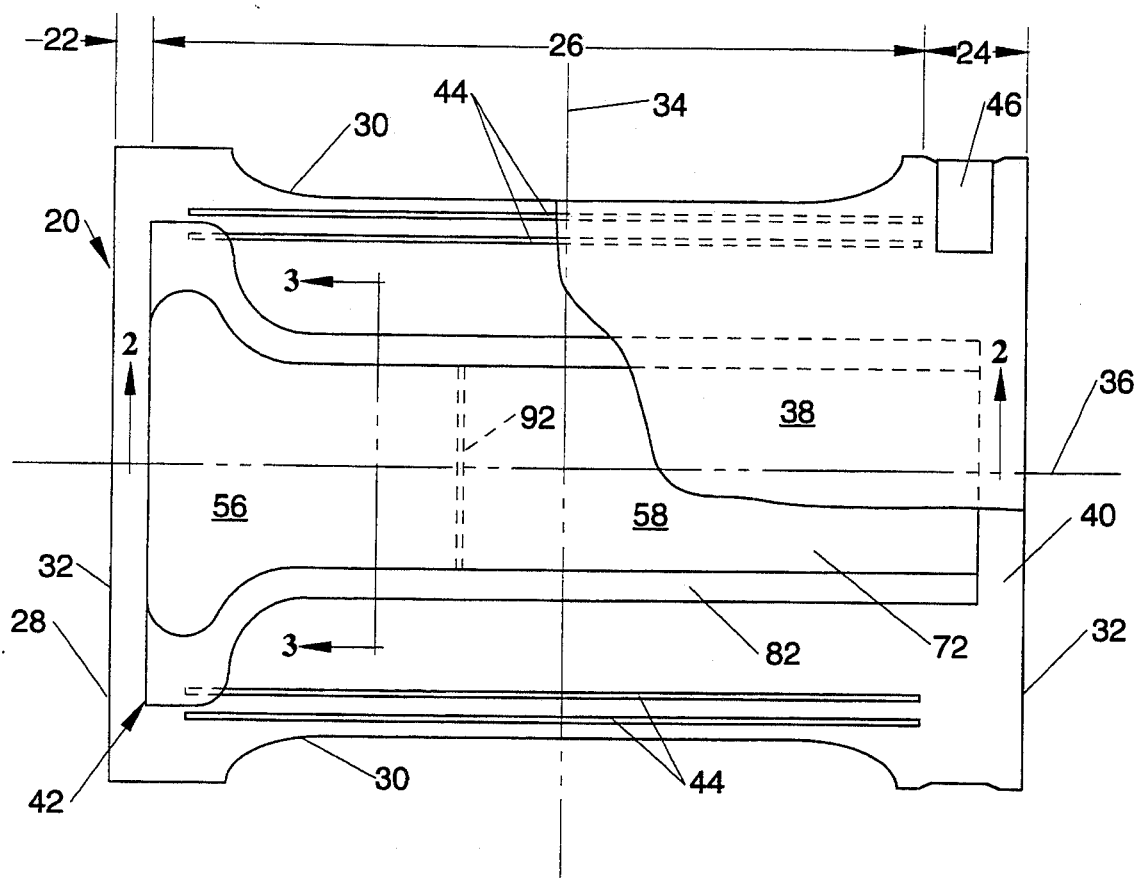
FIG. 1 is a plan view of a disposable diaper embodiment of the present invention wherein most of the topsheet has been cut-away to more clearly show the underlying absorbent member of the diaper.

The absorbent members of the present invention will be described herein in relationship to their use in disposable absorbent articles; however, it should be understood that the potential application of the absorbent members of the present invention should not be limited to disposable absorbent articles. As used herein, the term "disposable absorbent article" refers to articles which absorb and contain body exudates and more specifically refers to articles which are placed against or in proximity to the body of the wearer to absorb and contain the various exudates discharged from the body, and which are intended to be discarded after a single use (i.e., they are not intended to be laundered or otherwise restored or reused). A preferred embodiment of a disposable absorbent article, diaper 20, is shown in FIG. 1. As used herein, the term "diaper" refers to a garment generally worn by infants and incontinent persons that is worn about the lower torso of the wearer. It should be understood, however, that the present invention is also applicable to other disposable absorbent articles such as incontinent briefs, incontinent pads, sanitary napkins, and the like.

FIG. 1 is a plan view of the diaper 20 of the present invention in its flat-out, uncontracted state (i.e., with elastic induced contraction removed) with portions of the structure being cut-away to more clearly show the construction of the diaper 20 and with the portion of the diaper 20 which contacts the wearer facing the viewer. The diaper 20 is shown in FIG. 1 to have a front waistband region 22, a back waistband region 24, a crotch region 26 and a periphery 28 which is defined by the outer edges of the diaper in which the longitudinal edges are designated 30 and the end edges are designated 32. The diaper additionally has a transverse centerline which is designated 34 and a longitudinal centerline which is designated 36.

The diaper 20 preferably comprises a liquid pervious topsheet 38; a typically liquid impervious backsheet 40; an absorbent member 42; and elastic members 44. While the topsheet 38, the backsheet 40, the absorbent member 42, and the elastic members 44 may be assembled in a variety of well known configurations, a preferred diaper configuration is described generally in U.S. Pat. No. 3,860,003 entitled "Contractible Side Portions for Disposable Diaper", which issued to K. B. Buell on Jan. 14, 1975, and which patent is incorporated herein by reference.

Figure 2:
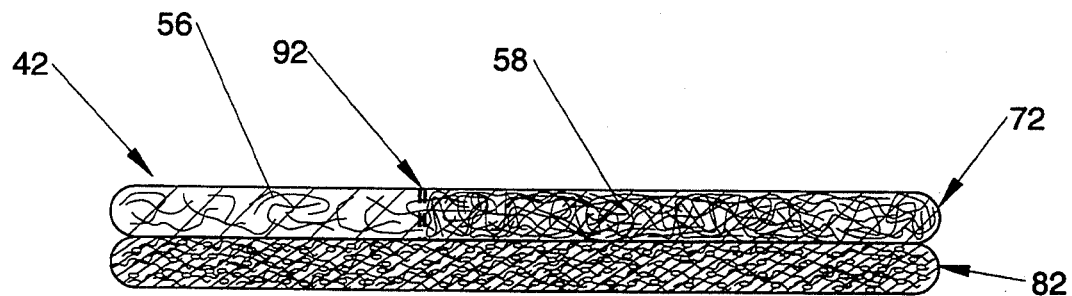
FIG. 2 is a longitudinal sectional view of only the absorbent member of the disposable diaper taken along sectional line 2—2 FIG. 1.
Figure 3:
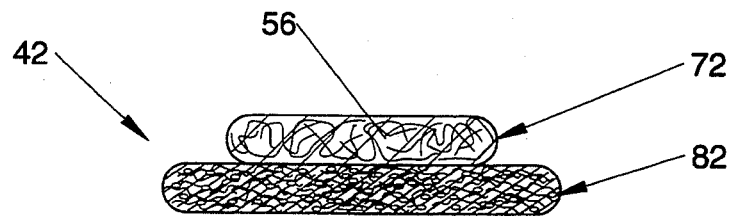
FIG. 3 is a transverse sectional view of only the absorbent member of the disposable diaper taken along sectional line 3—3 of FIG. 1.

FIG. 1 shows a preferred embodiment of the diaper 20 in which the topsheet 38 and the backsheet 40 are co-extensive and have length and width dimensions generally larger than those of the absorbent member 42. The topsheet 38 is associated with and superimposed on the backsheet 40 thereby forming the periphery 28 of the diaper 20. The periphery 28 defines the outer perimeter or the edges of the diaper 20. The periphery 28 comprises the end edges 32 and the longitudinal edges 30. FIGS. 2 and 3 are longitudinal and transverse, respectively, sectional views of only the absorbent member 42 shown in FIG. 1.

The diaper 20 has front and back waistband regions 22 and 24, respectively, extending from the end edges 32 of the diaper periphery 28 toward the transverse centerline 34 of the diaper a distance from about 2% to about 10%, preferably about 5%, of the length of the diaper 20. The waistband regions comprise those upper portions of the diaper 20, which when worn, encircle the waist of the wearer. The crotch region 26 is that portion of the diaper 20 between the waistband regions 22 and 24, and comprises that portion of the diaper 20 which, when worn, is positioned between the legs of the wearer and covers the lower torso of the wearer. Thus, the crotch region 26 defines the area of typical liquid deposition for a diaper 20 or other disposable absorbent article.

The topsheet 38 is compliant, soft feeling, and non-irritating to the wearer's skin. Further, the topsheet 38 is liquid pervious permitting liquids to readily penetrate through its thickness. A suitable topsheet 38 may be manufactured from a wide range of materials, such as porous foams, reticulated foams, apertured plastic films, natural fibers (e.g., wood or cotton fibers), synthetic fibers (e.g., polyester or polypropylene fibers) or from a combination of natural and synthetic fibers. Preferably, the topsheet 38 is made of a hydrophobic material to isolate the wearer's skin from liquids in the absorbent member 42.

A particularly preferred topsheet 38 comprises staple length polypropylene fibers having a denier of about 1.5, such as Hercules type 151 polypropylene marketed by Hercules, Inc. of Wilmington, Delaware. As used herein, the term "staple length fibers" refers to those fibers having a length of at least about 15.9 mm (0.62 inches).

There are a number of manufacturing techniques which may be used to manufacture the topsheet 38. For example, the topsheet 38 may be woven, non-woven, spunbonded, carded, or the like. A preferred topsheet is carded, and thermally bonded by means well known to those skilled in the fabrics art. Preferably, the topsheet 38 has a weight from about 18 to about 25 grams per square meter, a minimum dry tensile strength of at least about 400 grams per centimeter in the machine direction and a wet tensile strength of at least about 55 grams per centimeter in the cross-machine direction The backsheet 40 is typically impervious to liquids and is preferably manufactured from a thin plastic film, although other flexible liquid impervious materials may also be used. The backsheet 40 prevents the exudates absorbed and contained in the absorbent member 42 from wetting articles which contact the diaper 20 such as bed sheets and undergarments. Preferably, the backsheet 40 is polyethylene film having a thickness of from about 0.012 mm (0.5 mil) to about 0.051 millimeters (2.0 mils), although other flexible, liquid impervious materials may be used. As used herein, the term "flexible" refers to materials which are compliant and which will readily conform to the general shape and contours of the wearer's body.

A suitable polyethylene film is manufactured by Tredegar Industries, Inc. of Terre Haute, Ind. under the designation RR8220 blend for blown films and RR5475 blend for cast films. The backsheet 40 is preferably embossed and/or matte finished to provide a more clothlike appearance. Further, the backsheet 40 may permit vapors to escape from the absorbent member 42 while still preventing exudates from passing through the backsheet 40.

The size of the backsheet 40 is dictated by the size of the absorbent member 42 and the exact diaper design selected. In a preferred embodiment, the backsheet 40 has a modified hourglass-shape extending beyond the absorbent member 42 a minimum distance of at least about 1.3 centimeters to about 2.5 centimeters (about 0.5 to about 1.0 inch) around the entire diaper periphery 28.

The topsheet 38 and the backsheet 40 are joined together in any suitable manner. As used herein, the term "joined" encompasses configurations whereby the topsheet 38 is directly joined to the backsheet 40 by affixing the topsheet 38 directly to the backsheet 40, and configurations whereby the topsheet 38 is indirectly joined to the backsheet 40 by affixing the topsheet 38 to intermediate members which in turn are affixed to the backsheet 40. In a preferred embodiment, the topsheet 38 and the backsheet 40 are affixed directly to each other in the diaper periphery 28 by attachment means (not shown) such as an adhesive or any other attachment means as known in the art. For example, a uniform continuous layer of adhesive, a patterned layer of adhesive, or an array of separate lines, spirals, or spots of adhesive may be used to affix the topsheet 38 to the backsheet 40.

Tape tab fasteners 46 are typically applied to the back waistband region 24 of the diaper 20 to provide a fastening means for holding the diaper on the wearer. Only one of the tape tab fasteners is shown in FIG. 1. The tape tab fasteners 46 can be any of those well known in the art, such as the fastening tape disclosed in U.S. Pat. No. 3,848,594 issued to K. B. Buell on Nov. 19, 1974, which patent is incorporated herein by reference. These tape tab fasteners 46 or other diaper fastening means, such as pins, are typically applied near the corners of the diaper 20.

The elastic members 44 are disposed adjacent the periphery 28 of the diaper 20, preferably along each longitudinal edge 30, so that the elastic members 44 tend to draw and hold the diaper 20 against the legs of the wearer. Alternatively, the elastic members 44 may be disposed adjacent either or both of the end edges 32 of the diaper 20 to provide a waistband as well as or rather than leg cuffs. For example, a suitable waistband is disclosed in U.S. Pat. No. 4,515,595 issued to David J. Kievit and Thomas F. Osterhage on May 7, 1985, which patent is herein incorporated by reference. Another suitable waistband structure is one which incorporates elastic waist features to provide a dynamic fit about the wearer well as improved containment characteristics. Such a waistband structure is disclosed in U.S. Pat. No. 5,151,092 issued to Kenneth Buell, Sandra H. Clear, and Danielia T. Falcone on Sep. 29, 1992, which patent is herein incorporated by reference. In addition, a method and apparatus suitable for manufacturing a disposable diaper having elastically contractible elastic members is described in U.S. Pat. No. 4,081,301 entitled "Method and Apparatus for Continuously Attaching Discrete, Stretched Elastic Strands to Predetermined Isolated Portions of Disposable Absorbent Products" which issued to K. B. Buell on Mar. 28, 1978 and which patent is incorporated herein by reference.

The elastic members 44 are secured to the diaper 20 in an elastically contractible condition so that in a normally unrestrained configuration, the elastic members 44 effectively contract or gather the diaper 20. The elastic members 44 can be secured in an elastically contractible condition in at least two ways. For example, the elastic members 44 may be stretched and secured while the diaper 20 is in an uncontracted condition. Alternatively, the diaper 20 may be contracted, for example, by pleating, and the elastic members 44 secured and connected to the diaper 20 while the elastic members 44 are in their unrelaxed or unstretched condition.

In the embodiment illustrated in FIG. 1, the elastic members 44 extend essentially the entire length of the diaper 20 in the crotch region 26. Alternatively the elastic members 44 may extend the entire length of the diaper 20, or any other length suitable to provide an elastically contractible line. The length of the elastic members 44 is dictated by the diaper's design.

The elastic members 44 may take a multitude of configurations. For example, the width of the elastic members 44 may be varied from about 0.25 millimeters (0.01 inches) to about 25 millimeters (1.0 inch) or more; the elastic members 44 may comprise a single strand of elastic material or may comprise several parallel or non-parallel strands of elastic material; or the elastic members 44 may be rectangular or curvilinear. Still further, the elastic members 44 may be affixed to the diaper in any of several ways which are known in the art. For example, the elastic members 44 may be ultrasonically bonded, heat and pressure sealed into the diaper 20 using a variety of bonding patterns or the elastic members 44 may simply be glued to the diaper 20.

The absorbent member 42 is positioned between the topsheet 38 and the backsheet 40 to form the diaper 20. The absorbent members of the present invention are fibrous webs or batts which comprise both entangled masses of fibers and particles of absorbent gelling material. The absorbent member 42 is generally compressible, conformable, non-irritating to the wearer's skin, and capable of absorbing and retaining liquids and certain body exudates. It should be understood that for purposes of this invention that an absorbent member comprises at least two structural elements or layers, but is not necessarily limited to two layers or sheets of materials. Thus, the absorbent member 42 may actually comprise laminates or combinations of several sheets or webs of the requisite types of materials as hereinafter described. Thus as used herein, the term "member" includes the term "members" or "layers" or "layered." In addition, each sheet or web (or member or layer) need not be formed of a single unitary piece of material, but may be formed of a number of smaller strips or components joined together lengthwise or width-wise, so long as they are in fluid communication with one another.

Figure 4:
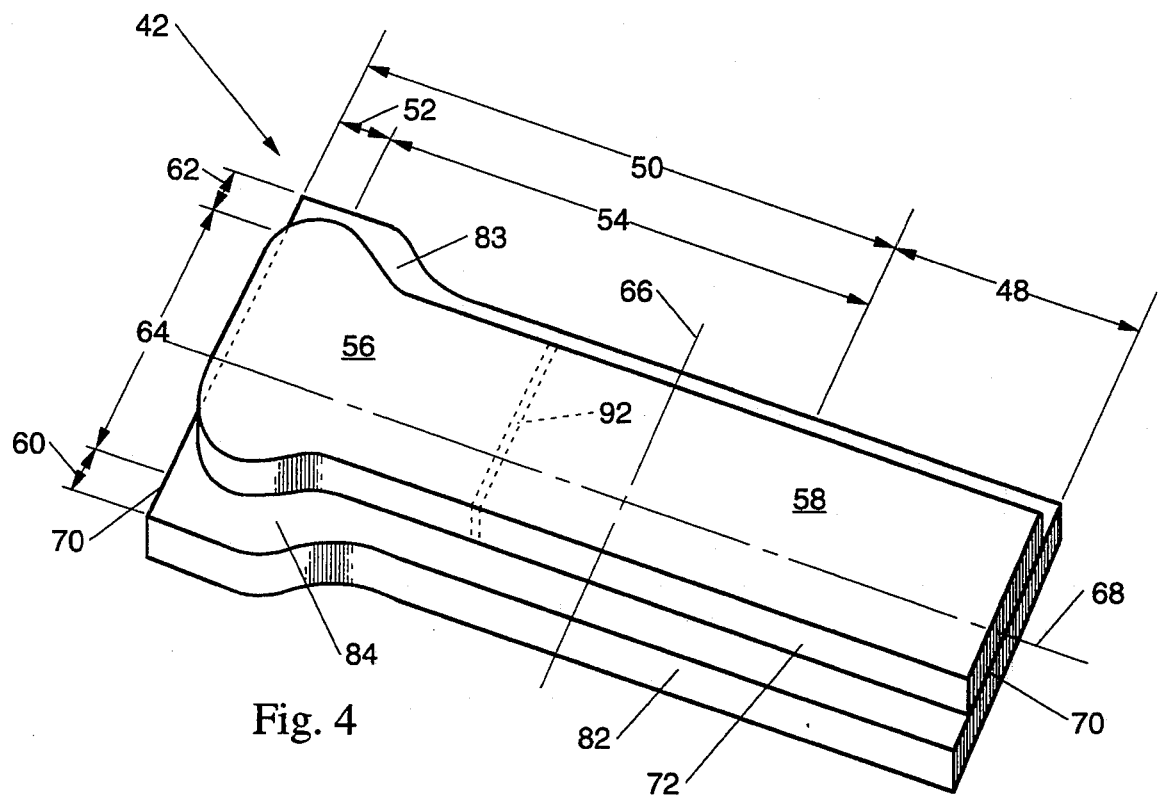
FIG. 4 is a perspective view of the absorbent member of the disposable diaper shown in FIG. 1.

FIG. 4 is a perspective view of a preferred embodiment of the absorbent member 42 of the present invention. As shown in FIGS. 1–5, the absorbent member 42 comprises an upper acquisition layer 72 and a lower storage layer 82. The upper acquisition layer further includes an acquisition zone 56 forward of the double-dotted line 92 (which represents a density interface) and a distribution zone 58. The lower storage layer 82 is shown in FIG. 4 to comprise a back section 48 and a front section 50. The front section 50 is shown to have an end region 52 and a deposition region 54. Further, the front section 50 is transversely divided into three regions comprising two transversely spaced ear regions 60 and 62 respectively, and a central region 64. The lower storage layer 82 additionally has a transverse centerline which is designated 66 and a longitudinal centerline which is designated 68.

The lowert storage layer 82 has a back section 48 and a front section 50 that is contiguous with the back section 48. The back section 48 and the front section 50 of the lower storage layer 82 extend respectively from the end edges 70 of the lower storage layer 82 toward the transverse centerline 66, the front portion 50 extending a distance from about one half to about three-fourths, preferably about two-thirds, of the length of the lower storage layer 82. The front section 50 is preferably greater than one half of the total length of the lower storage layer 82 so that it will encompass all of the area of typical liquid deposition of an absorbent member 42 when it is placed in a diaper or other absorbent article.

The front portion 50 has an end region 52 and a deposition region 54. The end region 52 comprises that portion of the front section 50 extending from the respective end edge 70 of the lower storage layer 82 toward the transverse centerline 66 a distance from about 2% to about 10%, preferably about 5%, of the length of the lower storage layer 82. The deposition region 54 comrpises that portion of the front portion 50 that is contiguous with and positioned between the end region 52 and the back section 48 and encompasses the area of typical liquid deposition of the absorbent member 42.

The front portion 50 further has two transversely spaced ear regions 60 and 62 respectively, and a central region 64 disposed intermediate the ear regions 60 and 62. The ear regions 60 and 62 comprise those portions which generally extend from the longitudinal edges 30 of the periphery 28 toward the longitudinal centerline a distance from about one-tenth to about one-third of the width of the lower storage layer 82. Thus, the ear regions 60 and 62 are those portions that engage the side marginal portions of the wearer's waist and torso, whereas the central region 64 engages the medial portion of the wearer's waist and torso. The central region thus defines the transverse area of typical liquid deposition.

The lower storage la82 may be manufactured in a wide variety of sizes and shapes (e.g., rectangular, hourglass, asymmetrical, etc.) and from a wide variety of materials. The total absorbent capacity of the lower storage layer 82 should, however, be compatible with the design liquid loading for the intended use of the absorbent article or diaper. Further, the size and absorbent capacity of the lower storage layer 82 may be varied to accommodate wearers ranging from infants through adults. The upper acquisition layer 72 preferably consists of a homogeneous composition of hydrophilic fibrous material which has been selectively densified. The lower storage layer 82 preferably consists of a mixture of hydrophilic fibrous material and particular amounts of discrete particles of absorbent gelling material having a particular particle size distribution, and preferably has a uniform density profile.

As shown in FIG. 4, there are preferably margins 83 and 84 from the side edge of the upper acquisition layer 72 to the side edge of the lower storage layer 82, at least in the area of typical liquid deposition. Such margins are preferably at least about 0.02 inches (0.5 cm), more preferably at least about 0.5 inches (1.25 cm), to minimize the likelihood of leakage caused by wicking fluid all the way to the edge of the absorbent member. The margins preferably extend for the full length of the absorbent member, although the margins could be maintained only in the most likely discharge regions for a particular wearer, such as toward the front edge for male wearers and more centrally for female wearers.

Various types of hydrophilic fibrous material can be used in in the upper acquisition layer 72 and lower storage layer 82 of the absorbent member 42. Any type of hydrophilic fibrous material which is suitable for use in conventional absorbent products are suitable for use in the absorbent member 42 of the present invention. Specific examples of such hydrophilic fibrous material include cellulose fibers, modified cellulose fibers, rayon, polyester fibers such as polyethylene terephthalate (DACRON), hydrophilic nylon (HYDROFIL), and the like. Other examples of suitable hydrophilic fibrous materials include hydrophilized hydrophobic fibers, such as surfactant-treated or silica-treated thermoplastic fibers derived, for example, from polyolefins such as polyethylene or polypropylene, polyacrylics, polyamides, polystyrenes, polyurethanes and the like. (These structures provide excellent wicking properties which are important in the present invention.) For reasons of availability and cost, cellulose fibers, in particular wood pulp fibers which are also referred to as airfelt, are preferred.

Other cellulosic fiber materials which may be especially useful in certain absorbent members herein are the stiffened, twisted, curled, cellulosic fibers which can be produced by internally cross-linking cellulose fibers with a cross-linking agent. Fibers of this general type are disclosed, for example, in Bernardin, U.S. Pat. No. 3,224,926, issued Dec. 21, 1965; Steiger, U.S. Pat. No. 3,241,553, issued Mar. 22, 1966; Chung, U.S. Pat. No. 3,440,135, issued Apr. 22, 1969; Steiger, U.S. Pat. No. 3,658,613, issued Apr. 26, 1972; Chatterjee, U.S. Pat. No. 3,932,209, issued Jan. 13, 1976 and Sangenis et al., U.S. Pat. No. 4,035,147, issued Jul. 12, 1977, all of which patents are incorporated herein by reference.

One type of stiffened, twisted, curled cellulose fibers useful as the hydrophilic fiber component of the absorbent members herein comprises cellulose fibers which have been internally cross-linked, for example with a $C_2$–$C_8$ dialdehyde, while such fibers are in a relatively dehydrated state. Such fibers can be defined in terms of their dry fiber and wet fiber twist counts (at least 4.5 twist nodes per millimeter dry and at least 0.5 twist node per millimeter less than that when wet and preferably also at least about 3.0 twist nodes per millimeter wet) and by their fluid retention characteristics (average isopropyl alcohol retention value of less than 30%; average water retention value of from 28% to 50%). Stiffened, twisted, curled cellulosic fibers of this type are described in greater detail in European Patent Publication No. 251,676, published Jan. 7, 1988, and in European Publication No. 252,650, published Jan. 13, 1988. Both of these published patent applications were filed in the name of The Procter & Gamble Company and both are incorporated herein by reference. In addition, U.S. Pat. No. 4,822,453, issued Apr. 18, 1989 to Dean et al., U.S. Pat. No. 4,888,093, issued Dec. 19, 1989 to Dean et and U.S. Pat. No. 4,898,642, issued Feb. 6, 1990 to Moore et al., also describe this cross-linking process in greater detail, as well as providing further discussion of quantifying the stiffness, twist, and curl imparted to the fibers, and are hereby incorporated herein by reference.

Another type of stiffened, twisted, curled cellulose fibers which are useful and presently preferred as the hydrophilic fiber component of the absorbent members herein comprises cellulose fibers which have been internally cross-linked, for example with a $C_2$–$C_9$ polycarboxylic acid cross-linking agent, such as citric acid, while such fibers are in a relatively dehydrated state. Such fibers can likewise be defined in terms of their dry fiber and wet fiber twist counts (at least 2.5 twist nodes per millimeter dry and at least 1.0 twice nodes per millimeter less than that when wet and preferably also at least about 1.5 twist nodes per millimeter wet) and by their fluid retention characteristics (average water retention value of from 28% to 50%). Stiffened, twisted, curled cellulosic fibers of this type are described in greater detail in U.S. Pat. No. 5,137,537, issued Aug. 11, 1992 to Carlisle M. Herron and David J. Cooper. which is hereby incorporated herein by reference.

While the hydrophilic fibrous material utilized in the lower storage layer 82 may comprise any one or more of the foregoing materials, in order to achieve the advantages of the present invention the upper acquisition layer 72 is preferably a homogenous composition of chemically stiffened, twisted, and curled cellulose fibers as described in the preceding paragraph. The lower storage layer 82 can be formed of these fibers but is preferably made of airfelt to minimize product cost since wicking ability is not a primary function of lower storage layer 82.

It may be desirable in some applications to include some quantity of hydrophobic fibrous material in the absorbent members of the present invention, particularly in the upper acquisition layer. Such hydrophobic fibrous materials may include synthetic fibers such as rayon, polyethylene, polypropylene, and polyethylene terephthalate fibers, for example, as well as bicomponent, tricomponent, and mixed fibers. The use of such hydrophobic fibrous materials, as well as hydrophilic and hydrophilized hydrophobic fibrous materials (synthetic or natural), is described in greater detail in the above-referenced and incorporated PCT Published Applications WO 91/11162, WO 91/11163, and WO 91/11165.

Other fibrous materials which may be suitable for inclusion include capillary channel fibers, such as those described in greater detail in European Patent Publication No. 391,814, published Oct. 10, 1990. This published application was filed in the name of the Eastman Kodak Company, and is hereby incorporated herein by reference.

Such additional fibrous materials, when of a hydrophobic nature, are preferably present in a comparatively small quantity, typically on the order of about 30% or less (total web weight basis) such that the web remains substantially hydrophilic. The addition of such hydrophobic fibrous materials to the absorbent members of the present invention may provide improved wicking properties, as well as improved capacity, structural integrity, and resiliency.

As used herein, the term "hydrophilic" describes fibers or the surfaces of fibers which are wetted by the liquids deposited onto the fibers. The state of the art respecting wetting of materials allows definition of hydrophilicity (and wetting) in terms of contact angles and the surface tension of the liquids and solids involved. This is discussed in detail in The American Chemical Society publication entitled *Contact Angle, Wetability, and Adhesion* edited by Robert F. Gould and copyrighted in 1964. A fiber or surface of a fiber is said to be wetted by a liquid either when the contact angle between the liquid and the fiber or surface is less than 90° or when the liquid will tend to spread spontaneously across the surface of the fiber; both conditions normally coexisting.

In addition to hydrophilic fibrous material, the lower storage layer 82 preferably contains particular amounts of discrete, preferably nonfragile, nonfibrous particles of absorbent gelling material. (Nonfibrous particles being used herein to designate a specific type of "particulate" material wherein the length to diameter ratio of such particulate material is about 10 or less.) Absorbent gelling materials are those materials which, upon contact with liquids, imbibe such liquids and thereby form hydrogels. In this manner, liquids discharged into the lower storage layers of the present invention can be acquired and held by the particles, thereby providing absorbent members with enhanced absorbent capacity and/or improved liquid retention performance.

The absorbent gelling material particles which are employed will generally comprise a substantially water-insoluble, slightly cross-linked, partially neutralized, hydrogel-forming polymer material. Such absorbent gelling materials can be prepared from polymerizable, unsaturated, acid-containing monomers. Thus, such monomers include the olefinically unsaturated acids and anhydrides which contain at least one carbon to carbon olefinic double bond. More specifically, these monomers can be selected from olefinically unsaturated carboxylic acids and acid anhydrides, olefinically unsaturated sulfonic acids and mixtures thereof.

Suitable unsaturated acidic monomers for use in preparing the absorbent gelling materials used in this invention include those listed in U.S. Pat. No. RE 32,649, issued to Kerryn A. Brandt, Stephen A. Goldman, and Thomas A. Inglin on Apr. 19, 1988 and entitled *"Hydrogel-Forming Polymer Compositions For Use In Absorbent Structures"*, which is incorporated herein by reference. Preferred monomers include acrylic acid, methacrylic acid, and 2-acrylamido-2-methyl propane sulfonic acid. Acrylic acid itself is especially preferred for preparation of the absorbent gelling material.

In the hydrogel-forming absorbent gelling material the polymeric component formed from unsaturated, acid-containing monomers may be grafted onto other types of polymer moleties such as starch or cellulose. Acrylic acid grafted starch materials of this type are also especially preferred for use herein.

Preferred absorbent gelling materials which can be prepared from conventional types of monomers include hydrolyzed acrylonitrile grafted starch, acrylic acid grafted starch, polyacrylates, maleic anhydride copolymers and combinations thereof. Especially preferred are the polyacrylates and acrylic acid grafted starch.

Whatever the nature of the basic polymer components of the absorbent gelling materials used in the storage layers herein, such materials will in general be slightly cross-linked. Cross-linking serves to render the absorbent gelling materials used in this invention substantially water-insoluble, and cross-linking thus in part determines the gel volume and extractable polymer characteristics of the hydrogels formed from the absorbent gelling material employed. Suitable cross-linking agents are well known in the art and include, for example, those described in greater detail in U.S. Pat. No. 4,076,663, which issued to Masuda et al. on Feb. 28, 1978, and which is incorporated herein by reference. Preferred cross-linking agents are the di- or polyesters of unsaturated mono-or polycarboxylic acids with polyols, the bisacrylamides and the di-or triallyl amines. Especially preferred cross-linking agents are N,N'-methylenebisacrylamide, trimethylol propane triacrylate and triallyl amine. The cross-linking agent can generally comprise from about 0.001 mole percent to 5 mole percent of the resulting absorbent gelling material. More preferably, the cross-linking agent will comprise from about 0.01 mole percent to 3 mole percent of the absorbent gelling material used herein.

The slightly cross-linked, absorbent gelling materials which may be used in the structures of the present invention are generality employed in their partially neutralized form. For purposes of this invention, such materials are considered partially neutralized when at least 25 mole percent, and preferably at least 50 mole percent of monomers used to form the polymer are acid group-containing monomers which have been neutralized with a salt-forming cation. Suitable salt-forming cations include alkali metal, ammonium, substituted ammonium and amines. This percentage of the total monomers utilized which are neutralized acid group-containing monomers is referred to herein as the "degree of neutralization." Degree of neutralization will preferably not exceed 98%.

The absorbent gelling materials used in the storage layers herein must have a relatively high capacity for imbibing fluids encountered in absorbent members. The absorbent capacity of such materials can be quantified by referencing the "gel volume" of the polymeric gelling agents which are to be selected for use in the present invention.

For purposes of this invention, gel volume can be defined in terms of the amount of synthetic urine absorbed by any given absorbent gelling material and is specified as grams of synthetic urine per gram of absorbent gelling material. Gel volume in synthetic urine can be determined by forming a suspension of about 0.1–0.2 parts of dried absorbent gelling material to be tested with about 20 parts of synthetic urine. This suspension is maintained at ambient temperature under gentle stirring for about 1 hour so that swelling equilibrium is attained. Using a procedure described in greater detail in the Test Methods section of the above-referenced U.S. Pat. No. RE 32,649, the gel volume of the absorbent gelling material in grams of synthetic urine per gram of absorbent gelling material is then calculated from the weight fraction of the absorbent gelling material in the suspension and the ratio of the liquid volume excluded from the formed hydrogel to the total volume of the suspension. (The grams of absorbent gelling material or hydrogel-forming polymer being corrected to a dry weight basis in the calculation of the gel volume.)

The storage layers of the present invention, and especially the ones which are to be used in diapers, adult incontinence products or training pants, will generally employ absorbent gelling material having a gel volume of at least about 20 grams of synthetic urine per gram of absorbent gelling material. When the storage )ayers herein are constructed from cellulosic fibers such as wood pulp fibers, it may be desirable to utilize absorbent gelling material having a somewhat higher gel volume, i.e., a gel volume between about 25 and 60 grams of synthetic urine per gram of gelling agent.

Storage layers constructed from certain types of cellulosic fiber material such as, for example, the stiffened, curled cellulosic fibers hereinbefore described may actually be more effective at absorbing fluid if absorbent gelling materials of somewhat lower gel vol umes are employed. Absorbent geling material of generally lower gel volume tends to form hydrogels of generally higher gel strength (as quantified by the shear modulus in the manner described in the hereinbefore-referenced U.S. Pat. No. 4,654,039). Thus, in storage layers wherein the hydrophilic fibers are stiffened, curled cellulose fibers, it may be preferable to employ absorbent gelling material having a gel volume of from about 20 to 35 grams of synthetic urine per gram of absorbent gelling material.

Another feature of the absorbent gelling materials which are especially useful in the storage layers herein relates to the level of extractable polymer material present in such absorbent gelling material. Extractable polymer levels can be determined by contacting a sample of absorbent gelling material with a synthetic urine solution for the substantial period of time (e.g., at least 16 hours) which is needed to reach extraction equilibrium, by then filtering the formed hydrogel from the supernatant liquid, and finally by then determining the polymer content of the flitrate. The particular procedure used to determine extractable polymer content of the absorbent gelling materials used herein is also set forth in the hereinbefore referenced U.S. Pat. No. RE 32,649. Absorbent gelling materials especially useful in the storage layers herein are those which have an equilibrium extractables content in synthetic urine of no more than about 17%, preferably no more than about 10% by weight of the absorbent gelling material.

Although most absorbent gelling materials will perform well in the lower storage layer 82 of the present invention, absorbent gelling materials having high gel strength are particularly useful. Gel strength must be such that the particles of absorbent gelling material do not deform and fill to an unacceptable degree the capillary void space in the lower storage layer 82, thereby inhibiting both absorbent capacity of the structure and fluid distribution throughout the structure.

Gel strength refers to the tendency of the particles of absorbent gelling material to deform or spread under stress once the particles absorb liquids. For a given type of absorbent gelling material, gel strength will generally decrease as the gel volume increases. It has been found that it is desirable to utilize a lower storage layer 82 whose polymer materials have as high a gel strength as possible consistent with the realization of absorbent gelling materials of acceptably high gel volume.

It has been found that gel strength, i.e., gel deformation tendency, (in the context of absorbent gelling materials incorporated into absorbent members and absorbent articles) correlates directly with the shear modulus of the absorbent gelling material. Accordingly, polymer materials of absorbent gelling material having sufficient gel strength can be appropriately characterized by specifying gel strength in terms% of the shear modulus of the particles of absorbent gelling material.

Shear modulus can be conventionally measured, for example, by a procedure which involves the use of a stress rheometer to determine the ratio of (a) stress applied to a given sample versus (b) the resulting strain exhibited by the sample. The absorbent gelling material sample tested in this manner is swollen to its gel volume with synthetic urine. Using a procedure described in greater detail in the above-referenced U.S. Pat. No. RE 32,649, which has been incorporated herein by reference, the stress/strain ratio is determined. The shear modulus of the resulting sample in dynes/cm$^2$ is then subsequently calculated from this ratio. Absorbent gelling materials which have been found to be particularly useful in the present invention exhibit a shear modulus of at east about 2,000 dynes/cm$^2$. More preferably, the absorbent gelling materials have a shear modulus within the range of about 2.500 to about 92,000 dynes/cm$^2$ and most preferably of from about 5,000 to about 35,000 dynes/cm$^2$.

An important feature of the present invention is the utilization of the above-described absorbent gelling materials in the storage layer in the form of nonfibrous, preferably nonfragile, particles having certain particle size characteristics. In particular, it has been discovered that an unexpected improvement in absorbent capacity, acquisition, and distribution within the absorbent member can be realized by incorporating absorbent gelling material into the particular storage layers of the present invention in the form of particles which are generally larger than those which have heretofore been conventionally employed. Generally, provision of particles of absorbent gelling material of this relatively larger size requires the use of one or more manufacturing or processing techniques which eliminate or reduce the amount of smaller, finer particles and/or create larger particles that are introduced, along with the fibrous material, into the storage layers herein. An upper limit on absorbent gelling material particle size can also be provided since gelling agent particles which are too large are less desirable from a consumer aesthetics standpoint.

Specifically, the storage layers according to the present invention preferably include absorbent gelling material particles of a selected mass median particle size and a certain particle size deviation from the mass median particle size. For purposes of the present invention, particle size is defined as the dimension of a particle which is determined by sieve size analysis. Further, for purposes of this invention, the mass median particle size of a given sample of absorbent gelling material particles is defined as the particle size which divides the sample in half on a mass basis. Further details on sieve size analysis and mass median particle size analysis can be found in the above-referenced U.S. Pat. No. 5,047,023.

The absorbent gelling material particles employed in the storage layer of the present invention preferably have a mass median particle size greater than or equal to about 400 microns. Preferably, the mass median particle size of the particles will be greater than or equal to about 420 microns. More preferably, the mass median particle size of the particles will be greater than or equal to about 500 microns. Because very large particles are less desirable from a consumer aesthetics viewpoint, the mass median particle size may have an upper limit such that the mass median particle size is expressed in terms of a range. Thus, preferred mass median particle sizes range from about 400 to about 1680 microns, more preferably from about 400 to about 1410 microns, most preferably from about 400 to about 1190 microns.

Preferably, the absorbent gelling material particles used will also have a certain maximum particle size deviation from the mass median particle size. In particular, it is preferred that no more than about 16% by weight of the absorbent gelling material particles have a particle size less than 200 microns and/or no more than about 16% by weight of these particles have a particle size greater than 1680 microns. More preferably, no more than about 16% by weight of these particles should have a particle size less than 210 microns and/or no more than about 16% by weight have a particle size greater than 1410 microns. Most preferably no more than about 16% by weight have a particle size greater than about 1190 microns.

In an especially preferred embodiment of the present invention, the particles of absorbent gelling material will have a mass median particle size greater than or equal to about 841 microns. Particles having a mass median particle size greater than or equal to about 841 microns are especially preferred for use in the present invention because they provide larger capillaries within the absorbent member to enhance planar wicking and are generally slower absorbing on a mass basis so as to provide higher gush capacity for the absorbent member. Preferably, the mass median particle size should range from about 841 microns to about 1680 microns, more preferably from about 841 microns to about 1410 microns, with a range from about 841 microns to about 1190 microns being most preferred. The particles of absorbent gelling material also, preferably, have a certain maximum size deviation from the mass median particle size. In particular, it is preferred that between 0% and about 20% by weight of the particles have a particle size less than about 841 microns. More preferably, between 0% and about 10%, and most preferably between 0% and about 5%, of the particles have a particle size less than about 841 microns.

Within the foregoing mass median particle size and particle size distribution limitations, it is possible to further identify preferred particle size characteristics for the gelling agent particles useful herein by means of standard sieve analyses. In a typical sieve analysis, a sample or plurality of gelling agent particles is sifted through a set number of screens of diminishino screen opening size and the weight percent of the sample retained on and/or passing through each screen is determined. Standard methods for making such sieve analyses have been established, for example, by the American Society for Testing Materials (ASTM). One such method employs a Ro-Tap testing sieve shaker (manufactured by W. S. Tyler, Inc.) and a series of screens identified by either U.S. Sieve Series or Tyler Standard Sieve Series designations. Determination of particle size distribution using such a technique is described greater detail in *Perry's Chemical Engineers' Handbook, Sixth Edition*, (McGraw-Hill Book Company, 1984) at pp. 21–13 to 21–19, which publication is incorporated herein by reference.

The absorbent gelling material particles can be adjusted to, or close to, the requisite particle size distribution by controlling the processing techniques used to prepare the absorbent gelling material. Frequently this will involve varying and monitoring the conditions under which the absorbent gelling material is polymerized, dried, chopped, ground and/or agglomerated. Once absorbent gelling material particles are formed by whatever process, further treatment such as screening may be required to remove particles which, if left in, would cause the absorbent gelling material particle component to fall outside of the hereinbefore-described particle size requirements.

Absorbent gelling material particles which are particularly well suited for use in the foregoing size ranges are interparticle cross-linked aggregates. Such aggregate particles are formed by joining together two or more previously independent precursor particles of the types set forth above by interparticle cross-linking agents applied thereto and subjected to conditions, while maintaining the physical association of the precursor particles, which are sufficient to react the interparticle cross-linking agent with the polymer material of the precursor particles to form cross-link bonds between the precursor particles that form the aggregate. Such aggregates, as well as methods forming them, are described in greater detail in U.S. Pat. No. 5,149,334, issued Sep. 22, 1992 to Lahrman et al., which patent is hereby incorporated herein by reference.

One preferred technique for preparing particles which are larger than those ordinarily prepared by absorbent gelling material polymerization-drying-chopping techniques involves agglomeration of smaller particles to produce larger agglomerates. Agglomeration techniques can thus be used to raise the mass median particle size of absorbent gelling material particles and to thereby provide particles in agglomerated form which are suitable for use in the storage layers herein. Agglomeration techniques are well known in the art and may or may not involve the use of moisture addition to smaller particles or the use of a binder or other type of agglomerating medium.

Absorbent gelling material particles used in the storage layers herein, whether or not in agglomerated form, should be nonfragile. For purposes of the present invention, such particles are nonfragile if they are stable enough to withstand the forces encountered in manufacture and/or use without breaking apart and completely separating into their smaller component particles. This means that the particles should be stable enough that they do not break apart into smaller particles to the extent that the resulting particles would fall outside the scope of the particle size limitations set herein.

The relative amount of hydrophilic fibrous material and particles of absorbent gelling material used in the lower storage layer 82 of the present invention can be most conveniently expressed in terms of a weight percentage of the lower storage layer 82. The lower storage layer 82 preferably contains from about 2% to about 60%, more preferably from about 30% to about 60%, and most preferably about 40% by weight, of the lower storage layer 82 of absorbent gelling material. This concentration of absorbent gelling material can also be expressed in terms of a weight ratio of fiber to particulate. These ratios may range from about 40:60 to about 98:2. For most large particle absorbent gelling materials, the optimum fiber-to-particulate weight ratio is in the range of from about 40:60 to about 70:30. Based on a cost/performance analysis, a ratio of about 60:40 is presently most preferred for use in the lower storage layer 82.

In addition, the particles of absorbent gelling material may be dispersed in various weight ratios throughout different regions and thicknesses of the lower storage layer 82. For example, the relatively large particles of absorbent gelling material may be disposed only in the deposition region 54 of the lower storage layer 82 and not in the back section 48 or the end region 52. However, due to the provision of and interaction with the upper acquisition layer 72, it is presently preferred that the lower storage layer 82 be of substantially uniform composition and construction.

When relatively large particles of absorbent gelling material are maintained in the lower storage layer 82, the particles help maintain an open capillary structure when the lower storage layer 82 is wetted so as to enhance transport of liquids away from the deposition region 54 to the rest of the lower storage layer 82. In addition, the acquisition rate of the lower storage layer 82 is enhanced because, it is believed, relatively large particles acquire liquid more slowly on a mass basis than small particles, such that gel blocking is minimized resulting in the gush capacity of the deposition region 54 being enhanced especially, it is believed, for subsequent loadings. Thus, at least the deposition region 54, and preferably the entire lower storage layer 82 contains a uniformly distributed mixture of hydrophilic fibrous material and relatively large particles of absorbent gelling material. It is most preferred that the particles are substantially uniformly dispersed (thoroughly dispersed) throughout the entire lower storage layer 82, although the relatively large particles may be distributed in regions or zones which have higher concentrations of particles of absorbent gelling material than do other regions or zones. For example, there may be a concentration gradient along the thickness dimension with either the lowest concentration being at or near the surface of the storage layer which receives liquids (i.e., the top surface) or with the highest concentration being at or near the top surface of the storage layer, especially in the deposition region.

The upper acquisition layer 72 comprises an acquisition zone 56 and a distribution zone 58 in liquid communication with at least a portion of the acquisition zone 56. The acquisition zone 56 overlies at least a portion of the deposition region 54 forward of the double-dotted line 92 in FIGS. 1-5. The distribution zone 58 generally comprises the remainder of the upper acquisition layer 72.

It has been found that a relative capillarity difference between the acquisition zone 56 and the distribution zone 58 is of importance in the overall efficiency and effectiveness of the entire absorbent member 42. While liquid capillarity can be defined in several ways (e.g., pore size, density, basis weight, etc.), the density and basis weight of the structure are the preferred parameters to define liquid capillarity in the upper acquisition layer 72 of the present invention. Thus, the acquisition zone 56 must have both a relatively lower average density and lower average basis weight per unit area than the distribution zone 58 to establish the preferred capillary force gradient between them. Thus, the ratio of the average density of the distribution zone 58 to the average density of the acquisition zone 56 should preferably be about equal to or greater than about 2:1, more preferably about 2.5:1, and most preferably about 3:1.

Without wishing to be bound by theory, it is believed that the differential lower capillarity, the lower average density and lower average basis weight, of the acquisition zone 56 in comparison to the distribution zone 58 is significant in achieving both a more optimized liquid acquisition rate into the lower storage layer 82 and a relatively high liquid wicking rate throughout the absorbent member 42. When the distribution zone 58 is densified, the liquid wicking rate becomes much faster. It is believed that densifying the distribution zone 58 results in better wicking of liquid throughout the distribution zone 58 (the x-y direction) because of the higher capillary force due to the smaller pore size of the densified fibers. Densifying the distribution zone 58 further results in a reduction in the bulk of the structure (which is desirable from a consumer standpoint for aesthetic reasons).

With regard to the use of absorbent gelling material in the deposition region 54, it is believed that as higher amounts of absorbent gelling material are located in the area of typical liquid deposition, a maximum gel blocking effect is achieved, thereby reducing the liquid acquisition rate. Thus, it is important to provide a means for distributing the liquid throughout the lower storage layer 82 at a high rate. The acquisition zone 56 of lower average density and lower average basis weight per unit area than the lower storage layer 82 or distribution zone 58 provides such a means by ensuring that the liquid is introduced into lower storage layer 82 via a comparatively widespread area rather than a small area or point of introductiont Because the lower storage layer 82 is preferably substantially uniform in composition and construction, introduction of fluid over such a widespread area in an approximately equal distribution via upper acquisition layer 72 results in maximum utilization of the storage capacity of the lower storage layer 82 while minimizing the incidence of gel blocking.

The capillary force gradient created at the interface between the acquisition zone 56 and the distribution zone 58 also improves the containment characteristics of the absorbent member 42. Liquids deposited on the acquisition zone 56 tend to be acquired quickly into the structure by the action of the acquisition zone 56. Because the distribution zone 58 has a higher capillarity than the acquisition zone 56, the acquired liquids tend to be drawn into the distribution zone 58 and are then delivered to the other portions of the distribution zone 58 by the enhanced wicking rate achieved in the densified distribution zone 58.

The following discussion describes in more detail the enhanced wicking phenomenon which is believed to be an important feature in the present invention:

The fibers in the lower density region of the acquisition layer are less restrained than the fibers in the higher density region. Fibers stiffened by cross-link bonds partially untwist and uncurl upon wetting. These fibers remain stiff upon wetting and do not collapse as do conventional unstiffened fibers. This creates a permanent structure to continue to acquire and distribute fluid. Upon wetting, the web containing these cross-linked fibers expands. Fibers in the higher density portion of the acquisition layer expand considerably more than fibers in the lower density region of the acquisition layer. The cross-linked fibers partially untwist and uncurl upon wetting to create a situation for fluid propagation due to the untwisting and uncutling of the fibers.

Because of this fluid movement within the web containing the cross-linked cellulose fibers, the structure is said to "wick" the fluid. The degree of wicking can be controlled by the amount of cross-linking agent used to cross-link the cellulose fibers. Wicking is also controlled by physically altering the structsre via the degree of compression imparted to the cross-linked fibers in the structure. The higher the density, the more the structure is able to propagate the fluid due to the fibers being in a more restrained configuration than they would be in a lower density situation.

In the higher density "densified" region of the acquisition layer, herein called the distribution zone, the cross-linked fibers have more stored "potential energy" than do the cross-linked fibers in the lower density region of the acquisition layer, herein called the acquisition zone. Potential energy is used herein to describe the property that twisted and curled fibers have in the dry state which is released in the form of partial untwisting and uncutling when wetted. When the lower density region (acquisition zone) and the higher density region (distribution zone) are placed in fluid communication with one another, the density interface created between the two regions provides a capillary force gradient for enhanced fluid propagation across the boundary.

While both regions of the acquisition layer are capable of both acquiring and distributing fluid, the specific combination of lower and higher density regions within the same structure creates a more efficient and effective way to utilize the cross-linked fiber structure in combination with a storage core. The higher density region, the distribution zone, functions to quickly suction fluid away from the lower density region, the acquisition zone, and redistributes the fluid throughout the remainder of the acquisition layer. This wicking process serves to free the acquisition zone for subsequent fluid loadings, and provides a diffusing effect to introduce the fluid to the storage layer over a comparatively wider area. Although the lower density acquisition zone has a finite density, because it remains substantially free of fluid after passing fluid on to the distribution zone the incoming fluid is attracted to the acquisition zone as though it were in effect a hole or sink, resulting in continued rapid acquisition of fluid into the absorbent member.

This wicking behavior is crucial to successful performance of the absorbent member when incorporated into an absorbent article. Invariably, when such an article is worn by an individual, the absorbent member when viewed from either side assumes somewhat of a "U" shape, with the ends of the absorbent member elevated above the crotch region when the wearer is in an upright position. When the wearer is lying down on his or her back, or particularly when lying on his or her stomach, one end of the absorbent member is elevated above the region of liquid deposition. Even when the wearer is lying on his or her side, at least about one-half of the absorbent member is elevated above the region of liquid deposition.

The natural tendency of liquids is to flow downward under the influence of gravity, and this tendency often results in the regions of the absorbent member above the region of liquid deposition receiving little or no fluid to store while the regions below the deposition region are filled to capacity or beyond. The challenge is thus to combat the effects of gravity and transport fluid "uphill" to whatever regions of the absorbent article are located above the deposition region.

Absorbent members according to the present invention accomplish this critical function through the incorporation of an acquisition layer preferably consisting solely of stiffened, twisted, and curled cellulose fibers which overlies a storage layer having a comparatively high concentration of particles of absorbent gelling material. Through the use of a density gradient across the boundary between the acquisition and distribution zones, as well as the densification of the distribution zone, the acquisition layer is able to actually wick or pump the fluid uphill to regions of the absorbent member which are higher than the deposition region when worn by an individual. The storage capacity of substantially the entire storage layer is thus accessible to the fluid and capable of being utilized, thus greatly improving the performance and efficiency of the absorbent article as a whole.

Figure 5:
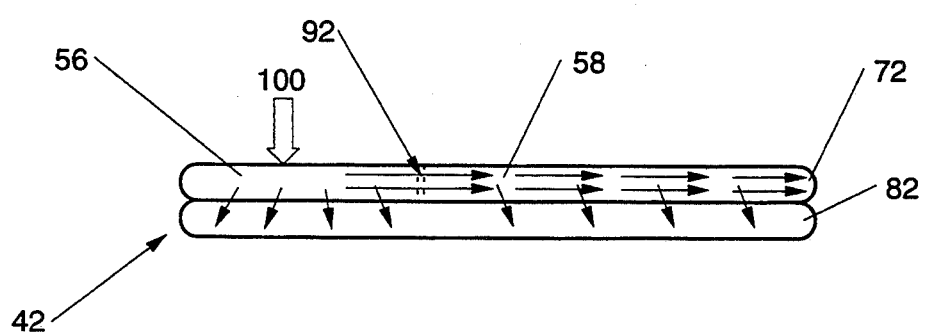
FIG. 5 is a transverse sectional view similar to FIG. 3, schematically illustrating typical fluid flow within the absorbent member.

FIG. 5 illustrates schematically the typical fluid transport phenomena associated with absorbent members 42 according to the present invention. A typical discharge of fluid is introduced into acquisition zone 56 as shown by the arrow labeled 100, where its descent is slowed by the fibrous material of the acquisition zone 56. Some of the fluid moves downward into the lower storage layer 82, but a substantial amount of the fluid is drawn across the double-dotted line 92, which represents the density discontinuity or interface between the two zones, and into the distribution zone, where it is distributed and introduced into the remainder of lower storage layer 82 over a wide area. The storage capacity of lower storage layer 82 is thus more effectively utilized, while the acquisition zone 56 is freed to acquire the next potential insult of fluid.

The lower storage layer 82, due to the utilization of the particles of absorbent gelling material, then stores and contains the fluid. These particles retain the stored fluid under even moderate pressure occurring during normal wear of the absorbent article. Therefore, fluid acquired by the upper acquisition layer and stored by the lower storage layer is positively contained and prevented from escaping to surrounding materials. Thus, it has been found that an upper acquisition layer 72 with an acquisition zone 56 having a lower average density and lower average basis weight per unit area than the distribution zone 59 improves leakage containment by more quickly acquiring and distributing liquids into and throughout the absorbent member 42.

While for simplicity FIG. 5 depicts the acquisition layer and storage layer in a planar configuration analogous to FIGS. 1-4, the schematic representation of fluid flow within the absorbent member has been found to perform as depicted even when formed into a "U" shape such as encountered in actual use.

In addition, it is believed that the acquisition zone 56 provides an additional mechanism whereby an absorbent member 42 that has already been wetted may contain and more readily acquire further discharged liquids. A property of the chemically stiffened, twisted, and curled cellulose fibers is that they expand when wetted. Thus when the upper acquisition layer 72 is wetted, the chemically stiffened, twisted and curled cellulose fibers in both the acquisition zone 56 and the distribution zone 58 expand. However, because there is a greater number of chemically stiffened, twisted and curled cellulose fibers per unit volume in the higher average density and higher average basis weight distribution zone 58, and because such fibers are more tightly compressed in the distribution zone 58, the distribution zone 58 tends to expand to a greater thickness than the acquisition zone 56. Thus, if the acquisition zone 56 is at least partially laterally surrounded by the distribution zone 58, a well or hole effect is created. This "well" is advantageous for second depositions of liquids because the liquids will tend to be drawn into the well because it is in effect a zero density acquisition area. This is especially helpful in the case of diapers for overnight use wherein the wearer sleeps on the stomach because gravity additionally tends to pull the later discharged liquids into the well whereupon they distribute into the acquisition zone 56 and are wicked into the distribution zone 58. Thus, the acquisition zone 56 provides an additional advantage for wetted absorbent members. Depending upon the configuration of the upper acquisition layer 72, this well or hole effect can also be utilized to aid in the containment and isolation of moist or runny bowel movements.

As depicted in FIGS. 1-5, in a presently preferred configuration the acquisition zone comprises the entire upper acquisition layer forward of the density interface, which extends generally transversely across the acquisition layer and divides or sections the acquisition layer along a preferably generally straight line. The distribution zone then comprises the entire upper acquisition layer rearward of the density interface.

This configuration maximizes the front-to-rear driving force exerted on the transported fluid and increases the wicking ability of the acquisition layer in transporting fluid to the rear portion of the lower storage layer. If the acquisition zone were surrounded by a portion of the distribution zone, some fluid would be drawn outward toward the edges of the lower storage layer, rather than the comparatively large rear portion, resulting in increased leakage potential and a failure to fully utilize the maximum available wicking capability of the selectively densified acquisition layer.

The distribution zone 58 is thus the relatively high capillarity (higher density and higher basis weight) portion of the upper acquisition layer 72. The primary functions of the distribution zone 58 are to absorb discharged liquids that are either deposited directly onto the distribution zone 58 or transferred to the distribution zone 58 via the capillary force gradients established between the acquisition zone 56 and the distribution zone 58, and to retain such liquids under the pressures encountered as a result of the wearer's movements.

The lower storage layer 82 preferably has a relatively high density and a high basis weight in relation to the acquisition zone 56. The density and basis weight values of the lower storage layer 82 include the weight of the particles of absorbent gelling material, such that the density and basis weight values will vary depending upon the amount of particles dispersed throughout the lower storage layer 82. Thus, the lower storage layer with generally have a density of from about 0.06 to about 0.4 g/cm$^3$, and more preferably within the range of from about 0.09 g to about 0.20 g/cm$^3$ for a lower storage layer 82 containing about 15% by weight of particles of absorbent gelling material. The basis weight of such a lower storage layer 82 can range from about 0.02 to about 0.186 g/cm$^2$, preferably from about 0.038 to about 0.12 g/cm$^2$. For a lower storage layer 82 containing about 50% by weight of particles of absorbent gelling material, the density will typically range from about 0.1 to about 0.68 g/cm$^3$ with a basis weight of from about 0.034 to about 0.31 g/cm$^2$. The density of the lower storage layer 82 is calculated from its basis weight and caliper measured on newly unpacked, unfolded and dissected diapers. The caliper is measured using a standard gauge with the sample under a "gentle" load of 10 g/cm$^2$. The basis weight is measured by die-cutting a certain size sample and weighing the sample on a standard scale, the weight and area of the sample determining the basis weight. (It should be noted that the density and basis weight values include the weiqht of the particles of absorbent gelling material.)

While the lower storage layer 82 may take on a number of sizes and shapes, it is preferred that the lower storage layer 82 is sized and shaped so as to substantially occupy the region between the topsheet and backsheet to provide maximum capacity for a given size of absorbent article. While the back section 48 and the end reDion 52 need not comprise storage zones, in the particularly preferred embodiment of the lower storage layer 82 as shown in FIGS. 2-5, the entire lower storage layer 82 is utilized for fluid storage.

As stated above, the lower storage layer 82 of the dual-layer absorbent core can be of any desired shape consistent with comfortable fit including, for example, circular, rectangular, trapezoidal, oblong, hourglass-shaped, dog-bone-shaped, or oval. If desired, the lower storage layer 82 can be wrapped in a high wet strength envelope web such as tissue paper or a synthetic fine pore, e.g., nonwoven material, to minimize the potential for particles of absorbent gelling material to migrate out of the lower storage layer 82. Another objective of such overwrapping is to desirably increase the in-use integrity of the dual layer absorbent core. Such a web can, in fact, be glued to the lower storage layer 82. Suitable means for carrying out this gluing operation include the glue spraying procedure described in U.S. Pat. No. 4,573,986 issued to Minetola and Tucker, on Mar. 4, 1986, which patent is incorporated herein by reference.

In a presently preferred embodiments, as shown in FIGS. 1-5, the shape of the lower storage layer 82 of the dual-layer absorbent core will be what can be described as a half-dog-bone shape. This shape provides good overall utilization of storage capacity while providing a comfortable fit for the wearer. In especially preferred embodiments, a lower storage layer 82 overwrapped with spray-glued tissue will be employed.

In the usual instance when the lower storage layer 82 generally defines the shape of the diaper or other absorbent article. the normal length of the backsheet 38 will be approached by the longest longitudinal dimension of the lower storage layer 82. However, in some applications (e.g. adult incontinence articles) wherein bulk reduction or minimum cost are important, the lower storage layer 82 would not take on the general shape of the diaper or incontinence structure. Rather it would be generally located to cover only the genital region of the wearer and could in this case have approximately the same top surface area as the upper acquisition layer 72. In this instance, both the upper acquisition layer 72 and the co-extensive lower storage layer 82 would be located toward the front of the article.

The acquisition zone 56 has a relatively lower capillarity and thus preferably a lower average density and a lower average basis weight per unit area than the distribution zone 58. The acquisition zone 56 serves to quickly collect and temporarily hold discharged liquids. Since such liquids are generally discharged in gushes, the acquisition zone 56 must be able to quickly acquire and transport liquid by wicking from the point of liquid contact to other parts of the absorbent member 42. The acquisition zone 56 preferably has a density of from about 0.03 to 0.24 g/cm$^3$, and more preferably from about 0.05 to about 0.15 g/cm$^3$. The basis weight of such an acquisition zone 56 will preferably range from about 0.015 to about 0.1 g/cm$^2$, and more preferably from about 0.018 to about 0.06 g/cm$^2$. The density of the acquisition zone 56 is calculated from its basis weight and caliper measured on newly unpacked, unfolded and dissected diapers. The caliper is measured using a standard gauge with the sample under a "gentle" load of 10 g/cm$^2$. The basis weight is measured by die-cutting a certain size sample and weighing the sample on a standard scale, the weight and area of the sample determining the basis weight. As discussed above, the ratio of the average density of the distribution zone 58 to the average density of the acquisition zone 56 should preferably be about equal to or greater than about 2:1, more preferably about 2.5:1, and most preferably about 3:1. Hence, for a given density and basis weight acquisition zone, the required density and basis weight of the distribution zone are fixed by these ratios. For example, if the density of the acquisition zone 56 were 0.07 g/cm$^3$, the density of the corresponding distribution zone 58 would be 0.21 g/cm$^3$, if a density ration of 3:1 were utilized.

While the acquisition zone 56 may conceivably have density and basis weight values equal to zero, i.e., a hole or void space, such an embodiment is not as preferred as an acquisition zone 56 having some minimal density and basis weight. The transfer of liquids through the topsheet 38 has been found to be diminished in an absorbent member 42 having an acquisition zone 56 of zero density and basis weight due to the lack of intimate contact between any fibers of the acquisition zone 56 and the topsheet 38. Thus, liquid may tend to pool or collect on the topsheet 38 thereby creating a wet feeling for the wearer. Thus, it is preferred that the acquisition zone 56 have some minimum density and basis weight.

While the density and basis weight of the acquisition zone 56 may vary throughout its area and thickness, such an embodiment is also not preferred. The acquisition zone 56 preferably has a substantially uniform density and uniform basis weight throughout its area and thickness. This uniform density and basis weight provides a uniform capillary force gradient across the interface between the acquisition zone 56 and the distribution zone 58 that provides even liquid transfer.

The shape, size and positioning of the acquisition zone 56 is of importance in determining the effectiveness of the resulting absorbent member 42 in rapidly acquiring discharged liquids. In accordance with the present invention, the acquisition zone 56 should be placed in a specific positional relationship with respect to the area of typical liquid deposition. While portions of the acquisition zone 56 may be positioned over the back section 48 of the lower storage layer 82, the acquisition zone 56 is preferably positioned generally over the front section 50 of the lower storage layer 82 so that the acquisition zone 56 is positioned in the area of typical liquid deposition, i.e., the deposition region 54. Thus, the acquisition zone 56 is placed in the vicinity of the point of discharge of liquids so as to be capable of quickly acquiring such liquids at their contact zone.

The generally forward positioning of the acquisition zone 56 can be defined by specifying the percentage of the top surface area of the acquisition zone 56 which is found forward of particular points along the length of the lower storage layer 82. While the positioning of the acquisition zone 56 can alternatively be defined with respect to the volume of the acquisition zone positioned forward of particular points, it has been found that the top surface area of the acquisition zone 56 is a more desirable definition because the top surface area actually defines the initial area available for liquid acquisition. In addition, since the thickness of the upper acquisition layer 72 is preferably uniform and the acquisition zone 56 has a generally rectangular cross-sectional area, the top surface area definition is equal to a volumetric definition in a preferred embodiment. Thus, the positioning of the acquisition zone 56 will be referenced throughout the specification as related to its top surface area. (i.e., The percentage of the top surface area of the acquisition zone positioned in a given area.)

Thus, in accordance with the present invention, at least a portion of the acquisition zone 56 is placed over the deposition region 54, even though the remaining portion may be positioned anywhere on the lower storage layer 82 including the back section 48 and the end regions 52. However, the acquisition zone 56 is preferably positioned relative to the lower storage layer 82 such that the top surface area of the acquisition zone 56 is completely positioned over the front section 50 of the lower storage layer 82. More preferably, the acquisition zone 56 is positioned relative to the lower storage layer 82 such that the top surface area of the acquisition zone 56 is completely positioned over the deposition region 54 of the lower storage layer 82. Even more preferably, at least 30% of the top surface area of the acquisition zone 56 is positioned over the front half of the front section (approximately the front ⅓ of the overall lower storage layer 82) of the lower storage layer 82.

The forward positioning of the acquisition zone 56 may alternatively be defined by specifying the percentage of the top surface area of the acquisition zone 56 that is found forward of particular points along the length of the diaper 20 or other absorbent article. Thus, the acquisition zone 56 is preferably positioned on the lower storage layer 82 relative to the backsheet 40 such that at least a portion of the top surface area of the acquisition zone 56 is in the crotch region 26 of the diaper 20. More preferably, the acquisition zone 56 is positioned such that its top surface area is completely positioned in the front two-thirds portion of the diaper 20, most preferably in the front half portion of the diaper 20; the top surface area also most preferably being completely positioned in the crotch region 26 of the diaper 20. (As noted herein, "portions" of the diaper 20 or other absorbent article can be defined by reference to the top surface area of the unfolded diaper 20 or absorbent article found in front of a given point on the line which defines the length of the diaper 20).

For purposes of determining the positioning of such acquisition zone 56, the length of the lower storage layer 82 or diaper 20 will be taken as the normal longest longitudinal dimension of the elongated structure. This normal longest dimension can be defined with respect to the structure as it is applied to the wearer. When worn, the opposing ends of the backsheet are fastened together so that the ends form a circle around the wearer's waist. The normal length of the lower storage layer 82 or diaper 20 will thus be the length of the line running through the lower storage layer 82 or diaper 20 from the point on the edge of it at the middle of the wearer's back waist, through the crotch, to the point on the opposite edge of the lower storage layer 82 or diaper 20 at the middle of the wearer's front waist.

The top surface area of the acquisition zone 56 may be found using either of two techniques. The primary and simplest way is to place the absorbent member 42 on a standard light box, such as the transluminator model manufactured by Aristo grid Lamp Products, Inc.. The acquisition zone 56, because it has a lower average density and lower average basis weight than the adjoining distribution zone 58, will appear lighter or brighter due to the fact that more light will be transmitted through the acquisition zone 56. The acquisition zone 56 can then be mapped onto paper having grids to measure the top surface area of the acquisition zone 56.

The alternative method comprises mapping the density profile of the upper acquisition layer 72 to determine the top surface area of the acquisition zone 56. The upper acquisition layer 72 is cut into samples having small areas. The density and basis weight of each of the samples are then calculated using the techniques discussed above. Thus, the relatively lower density and lower basis weight samples are charted against the relatively higher density and higher basis weight samples to measure the top surface area of the acquisition zone 56.

The acquisition zone 56 can be of any desired shape consistent with the absorbency requirements of the absorbent member 42 or diaper 20 including, for example, circular, rectangular, triangular, trapezoidal, oblong, hourglass-shaped, funnel-shaped, dog-bone-shaped, fox-shaped or oval. Preferred shapes of the acquisition zone 56 are those that increase the length of the interface between the acquisition zone 56 and the distribution zone 58 so that the relative capillarity difference between the zones are fully utilized. A presently preferred shape for the acquisition zone 56 is what may be described as a half-dog-bone shape, with the wider end facing toward the front of the absorbent member and the entire width of the narrower end adjoining the distribution zone 58, as shown particularly in FIGS. 1 and 4.

In addition, while the distribution zone 58 need not completely surround the acquisition zone 56 (i.e., it is in liquid communication with at least a portion of the lateral area of acquisition zone 56), in some embodiments of the present invention, the distribution zone 58 may partially or entirely laterally surround the acquisition zone 56 so as to take full advantage of the capillarity difference between the two zones.

The acquisition zone 56 may also have a number of different cross-sectional areas and configurations including those wherein the area of portions of the acquisition zone 56 is less or greater than its top surface area (i.e., the acquisition zone 56 is smaller or wider below the top surface of the upper acquisition layer 72.) For example, the acquisition zone 56 may have conical, trapezoidal, T-shaped or rectangular cross-sectional areas. As shown in FIGS. 2 and 3, the acquisition zone 56 preferably has a rectangular cross-sectional area so as to provide a uniform acquisition zone 56.

The acquisition zone 56 may have a different thickness than the adjoining distribution zone 58, and/or may not extend through the entire thickness of the upper acquisition layer 72. However, in a preferred embodiment as shown in FIGS. 2 and 3, the acquisition zone 56 preferably extends entirely through the thickness of the upper acquisition layer 72 and has a thickness equal to the thickness of the adjoining distribution zone 58.

While the acquisition zone 56 may be transversely positioned anywhere along the upper surface of the lower storage layer 82, it has been found that the acquisition zone 56 functions the most efficiently when it is transversely centered over the front section 50 or the deposition region 54 of the lower storage layer 82. Thus. the acquisition zone 56 is preferably centered about the longitudinal centerline 68 of the lower storage layer 82. More preferably, the acquisition zone 56 is transversely positioned only over the central region 64 of the front section 50 or deposition region 54 of the lower storage layer 82 such that none of the acquisition zone 56 is located over the ear regions 60 and 62.

Such an upper acquisition layer 72 is preferably made by airlaying a thickness profiled absorbent member-preform and then calendering the upper acquisition layer 72 in a fixed-gap calender roll to effect the selective densification of the upper acquisition layer 72 and establish the density gradient across the density interface 92. The thickness profiled upper acquisition layer 72 initially has areas of higher basis weight which define the distribution zone 58 and of lower basis weight which define the acquisition zone 56. The upper acquisition layer 72 is then calendered preferably to a uniform thickness. Thus, a lower average density and a lower average basis weight per unit area acquisition zone 56 is created relative to the higher average density and higher average basis weight distribution zone 58.

The resulting thickness of the acquisition layer 72 need not be uniform, however. Contoured calendar rolls, or other equally suitable methods, could be utilized which would result in different final thicknesses for the acquisition zone 56 and distribution zone 58. Establishing the density gradient at the density interface 92 is regarded as the critical factor in forming the upper acquisition layer 72. The uniform thickness calendaring is presently preferred because the uniform thickness of the two zones maximizes the contact area of the two zones at the density interface, i.e., the ratio of contact areas is 1:1.

Likewise, the lower storage layer 82 is preferably made by airlaying a uniform thickness absorbent member-preform. Additionally, discrete particles of absorbent gelling material are added to an air-entrained stream of fibers prior to their deposition onto the preform to affect uniform distribution of absorbent gelling material throughout the preformed lower storage layer 82. Thus, the resultant lower storage layer 82 preferably contains a uniform mixture of hydrophilic fibrous material and discrete particles of absorbent gelling material.

In use, the diaper 20 is applied to a wearer, by positioning the back waistband region 24 under the wearer's back, and drawing the remainder of the diaper 20 between the wearer's legs so that the front waistband region 22 is positioned across the front of the wearer. The ends of the tape-tab fasteners 46 are then secured preferably to outwardly facing areas of the diaper 20. In use, disposable diapers or other absorbent articles having such upper acquisition layers 72 having a relatively lower average density and lower average basis weight acquisition zone 56, tends to mole quickly acquire liquids into the acquisition zone 56 and to distribute these liquids to the remaining portions of the absorbent member 42 and to remain dry or dryer due to the preferential capillarity between the distribution zone 58 and the acquisition zone 56 of the upper acquisition layer 72 and the characteristics of the relatively large particles of absorbent gelling material in the lower storage layer 82.

Thus, such an absorbent member 42 helps to alleviate leakage around the edges of such absorbent articles.

As discussed above, the primary purpose of the upper acquisition layer 72 is to quickly collect and temporarily ho)d discharged liquids and to transport such liquids by wicking from the point of initial contact to other parts of the upper acquisition layer 72. Since the primary function of the upper acquisition layer 72 is to receive liquids passing through the topsheet 38 and to transport such liquids to other areas of the upper acquisition layer 72 and eventually onto the lower storage layer 82, the upper acquisition layer 72 is preferably entirely free of absorbent gelling material. Since the two functions, namely wicking and fluid storage, have been assigned to two different layers of the absorbent member, the performance of each can thus be optimized to achieve the best overall performance.

Alternatively, the upper acquisition layer 72 can contain small amounts of absorbent gelling material, but since the fluid transport and storage functions have been divided between the upper acquisition layer 72 and the lower storage layer 82, respectively, in the present invention it is preferred that no fluid storage take place in the upper acquisition layer 72. Hence, the use of absorbent gelling material in the upper acquisition layer is generally not preferred, as it tends to impede the wicking behavior of the stiffened, twisted, and curled cellulose fibers as they respond to the liquid infusion, and thus reduce the performance potential of the upper acquisition layer.

The overall shape and size of the upper acquisition layer 72 and its relationship to the lower storage layer 82 is of some importance in determining the effectiveness of the resulting diaper 20 or other absorbent article. The upper acquisition layer 72 in the unfolded configuration can be of any desired shape, for example, rectangular, oval, oblong, asymmetric or hourglass-shaped.

As shown in FIGS. 1 and 4, a presently preferred shape for the upper acquisition layer 72 is what may be described as a half-dog-bone shape, incorporating the half-dog-bone-shaped acquisition zone 56 and extending rearwardly toward the back waistband region of the absorbent article such that the distribution zone 58 is generally rectangular in shape. As such, the overall shape of the presently preferred upper acquisition layer 72 mimics the overall shape of the presently preferred lower storage layer 82.

The upper acquisition layer 72 of the present invention need not be as large as the lower storage layer 82 and preferably, in fact, has a top surface area which is substantially smaller than the top surface area of the lower storage layer 82. Generally, the upper acquisition layer 72 will have a top surface area from about 0.7 to about 1.0 times that of the lower storage layer 82. Most preferably, the top surface area of the upper acquisition layer 72 will be about 0.75 times that of the lower storage layer 82.

If the size of the upper acquisition layer 72 approaches the size of the lower storage layer 82, there is an increased likelihood that more fluid will be wicked to the edges of the storage layer than can be stored, hence resulting in an increased likelihood of leakage from the edges of the absorbent article. This is particularly true when fibrous materials having higher wicking rates are utilized, such as the stiffened, twisted, and curled cellulose fibers described above. The use of side margins 83 and 84, as shown in FIG. 4, helps to reduce the likelihood of leakage due to fluid being wicked to the edge of the absorbent member; hence, the difference in area between the upper acquisition layer and the lower storage layer preferably produces side margins, at least in the likely fluid discharge regions. On the other hand, if the upper acquisition layer 72 is too much smaller than the lower storage layer 82, the peripheral portions of the lower storage layer will not receive fluid and hence will not be utilized for storage.

The use of an upper acquisition layer which has a top surface area which is about 0.75 times that of the lower storage layer has been found to provide a good balance between leakage prevention and storage capacity utilization. For ease of assembly, it is also presently preferred that the upper acquisition layer and the lower storage layer have approximately the same nominal length and when assembled have generally aligned ends.

In order to provide sufficient acquisition capacity, it has been found that the top surface area of the acquisition zone 56 should comprise substantially less than the entire top surface area of the upper acquisition layer 72 of the dual-layer absorbent core. The top surface area (and/or volume) of the acquisition zone 56 preferably comprises less than about 50% of the top surface area (and/or volume) of the upper acquisition layer 72. More preferably, the top surface area of the acquisition zone 56 comprises less than about 35% of the top surface area of the upper acquisition layer 72 and most preferably about 30% of the top surface area of the upper acquisition layer 72. The positioning and area of the acquisition zone relative to the distribution zone may be tailored to accommodate the needs of particular wearers such as, for example, male or female, adult or child, and daytime wear versus nighttime wear.

While under some circumstances it may be possible or preferable to vary the pore size of the fibers in the upper acquisition layer without varying the density of the fibers to form acquisition and distribution zones, in upper acquisition layers according to the present invention such a variation would not generally be preferred. One possible way to vary the pore size of the fibers would be to utilize hardwood fluff with its smaller pore size for the acquisition zone and to utilize softwood fluff with its larger pore size for the distribution zone. The primary reason that such a variation would not generally be desirable is that hardwood fibers are generally shorter in length than softwood fibers. When the fibers are stiffened, twisted, and curled as described above, shorter fibers equate to less stored potential energy when the fibers are compressed, and hence less expansion, untwisting, and uncurling when fluids interact with the fibers. Without the use of the densification of the distribution zone, the corresponding increase in the stored potential energy therein would also not be achieved. Less stored potential energy translates into less wicking across the density interface, and the acquisition potential of absorbent members according to the present invention is not maximized.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A multi-layer absorbent member having a back section and a front section contiguous with said back section, said front section having an end region and a deposition region contiguous with said end region and said back section so that said deposition region is positioned between said end region and said back section, the absorbent member comprising:
   (a) at least one storage layer comprising a mixture of hydrophilic fibrous material and discrete particles of absorbent gelling material, said storage layer having a first top surface area; and
   (b) at least one acquisition layer positioend in fluid communication with said storage layer, said acquisition layer havinq a front edqe at least partially overlying said front section and a back edqe at least pattially overlying said back section, said acquisition layer further having two opposed side edqes extendinq between said front edge and said back edge, said acquisition layer comprising a homogeneous composition of hydrophilic fibrous material, said homogeneous composition comprising stiffened, twisted, and curled cellulose fibers, said acquisition layer comprising an acquisition zone for acquiring fluids having a first density and a first average basis weight, said acquisition zone being positioned at least pattially within said deposition region, said acquisition layer further comprising a densified distribution zone for distributing fluids in liquid communication with said acquisition zone at a density interface, said density interface extending generally transversely across said acquisition layer from one side edge to the opposite side edge, said distribution zone having a second average density which is at least about 2.0 times said first average density and a second average basis weight which is at least about 2.0 times said first average basis weight, and said acquisition layer having a second top surface area which is between about 0.7 and about 1.0 times said first top surface area;
   whereby fluid introouduced into siad acquisiton layer via said acquisition zone is drawn across said density interface and into said distribution zone via capillary action and subsequently distributed to said storage layer.

2. The absorbent member of claim 1, wherein said storage layer comprises between about 30% and about 60% by weight of said particles of absorbent gelling material.

3. The absorbent member of claim 2, wherein said storage layer comprises about 40% by weight of said particles of absorbent gelling material.

4. The absorbent member of claim 1, wherein said second average density is at least about equal to 2.5 times said first average density.

5. The absorbent member of claim 4, wherein said second average density is about equal to 3.0 times said first average density, and wherein said acquisition layer has a uniform overall thickness.

6. The absorbent member of claim 1, wherein said acquicition zone comprises less than about 50% of said second top surface area.

7. The absorbent member of claim 6, wherein said acquisition zone comprises less than about 35% of said second top surface area.

8. The absorbent member of claim 7, wherien said acquisiton zone comprises about 30% of said second top surface area.

9. The absorbent member of claim 1, wherein said acquisition layer consists essentially of a homogeneous composition of stiffened, twisted, and curled cellulose fibers.

10. The absorbent member of claim 1, wherein said particles of absorbent gelling material have a mass median particle size ranging from about 400 microns to about 1410 microns.

11. A multi-layer absorbent member having a back section and a front section contiguous with said back section, said front section having an end region and a deposition region contiguous with said end region and said back section so that said deposition region is positioned betwee said end region and said back section, the absorbent member comprising:
    (a) at least one storage layer comprising a mixture of hydrophilic fibrous material and discrete particles of absorbent gelling material having a mass median particle size ranging from about 400 microns to about 1410 microns, said storage layer having a first top surface area; and
    (b) at least one acquisition layer positioned in overlying spaced relation to said storage layer so as to be positioned between a wearer and said storage layer, said acquisition layer havinq a front edge at least partially overlying said front section and a back edqe at least partially overlying said back section, said acquisition layer further havinq two opposed side edges extending between said front edqe and said back edge, said acquisition layer comprising a homogeneous composition of hydrophilic fibrous material, said homogeneous composition comprising stiffened, twisted, and curled cellulose fibers, said acquisition layer comprising an acquisition zone for acquiring fluids having a first density and a first average basis weight, said acquisition zone being positioned at least partially within said deposition region, said acquisition layer further comprising a densified distribution zone for distributinq fluids in liquid communication with said acquisition zone at a density interface, said density interface extending generally transversely across said acquisition layer from one side edge to the opposite side edge, said distribution zone having a second average density which is about 3.0 times said first average density and a second average basis weight which is about 3.0 times said first average basis weight, and said acquisition layer having a second top surface area which is about 0.75 times said first top surface area, said acquisition zone comprising about 30% of said second top surface area, said acquisition layer further having a uniform overall thickness;
    whereby fluid introduced into said acquisition layer via said acquisition zone is drawn across said density interface and into said distribution zone via capillary action and subsequently distributed to said storage layer.

12. An absorbent article having a front waistband region, a back waistband region and a crotch region, said absorbent article comprising:
    (a) a backsheet; and
    (b) a multi-layer absorbent member positioned adjacent to said backsheet, said absorbent member comprising at least one storage layer comprising a mixture of hydrophilic fibrous material and discrete particles of absorbent gelling material, said storage layer having a first top surface area, said absorbent member further compri sing at least one acquisition layer positioned in fluid communication with said storage layer, said acquisition layer having a front edge generally adjacent to said front waistband region and a back edge generally adjacent to said back waistband region, said acquisition layer further having two opposed side edges extending between said front edge and said back edge said acquisition layer comprising a homogeneous composition of hydrophilic fibrous material, said homogeneous composition comprising stiffened, twisted, and curled cellulose fibers, said acquisition layer comprising an acquisition zone for acquiring fluids, said acquisition zone being positioned with respect to the absorbent article such that said acquisition zone is at least partially positioned in said crotch region, said acquisition zone having a first density and a first average basis weight, said acquisition zone being positioned in said deposition region, said acquisition layer further comprising a densified distribution zone for distributing fluids in 1iquid communication with said acquisition zone at a density interface, said density interface extending generally transversely across said acquisition layer from one side edge to the opposite side edge, said distribution zone having a second average density which is at leust about 2.0 times said first average density and a second average basis weight which is at least about 2.0 times said first average basis weight, and said acquisition layer having a second top surface area which is between about 0.7 and about 1.0 times said first top surface area; whereby fluid introduced into said acquisition layer via said acquisition zone is drawn across said density interface and into said distribution zone via capillary action and subsequently distributed to said storage layer.

13. The absorbent article of claim 12, wherein said storage layer comprises between about 30% and about 60% by weight of said particles of absorbent gelling material.

14. The absorbent article of claim 13, wherein said storage layer comprises about 40% by weight of said particles of absorbent gelling material.

15. The absorbent article of claim 12, wherein said second average density is at least about equal to 2.5 times said first average density.

16. The absorbent article of claim 15, wherein said second average density is about equal to 3.0 times said first average density, and wherein said acquisition layer has a uniform overall thickness.

17. The absorbent article of claim 12, wherein said acquisition zone comprises less than about 50% of said second top surface area.

18. The absorbent article of claim 17, wherein said acquisition zone comprises about 30% of said second top surface area.

19. The absorbent article of claim 12, wherein said absorbent article further comprises a topsheet associated with said backsheet such that said absorbent member is positioned between said topsheet and said backsheet.

20. The absorbent article of claim 12, wherein said particles of absorbent gelling material have a mass median particle size ranging from about 400 microns to about 1410 microns.

* * * * *

UNITED STATES PATENT AND TRADEMARK OFFICE
CERTIFICATE OF CORRECTION

PATENT NO. : 5,348,547
DATED : September 20, 1994
INVENTOR(S) : Michael Payne, et al It is certified that error appears in the above-indentified patent and that said Letters Patent is hereby corrected as shown below:

*Column 1, line 7, "invetion" should read —invention—.*

*Column 1, line 46, "Gelleft" should read —Gellert—.*

*Column 3, line 9, "utilizinq" should read —utilizing—.*

*Column 3, line 63, "havng" should read —having—.*

*Column 5, line 58, "denlet" should read —denier—.*

*Column 8, line 29, "lowert" should read —lower—.*

*Column 8, lines 48-49, "comrpises" should read —comprises—.*

*Column 8, line 67, "la82" should read —layer 82—.*

*Column 9, line 20, "0.02" should read —0.2—.*

*Column 10, line 31, "twice" should read —twist—*

*Column 11, line 68, "moleties" should read —moieties—.*

*Column 12, line 35, "generality" should read —generally—.*

*Column 13, line 13, ")ayers" should read —layers—.*

*Column 13, line 23, "vol umes" should read —volumes—.*

*Column 13, line 24, "geling" should read —gelling—.*

*Column 13, line 44, "flitrate" should read —filtrate—.*

*Column 14, line 10, "%" should be omitted.*

*Column 14, line 26, "east" should read —least—.*

*Column 14, line 28, "2.500" should read —2,500—.*

UNITED STATES PATENT AND TRADEMARK OFFICE
CERTIFICATE OF CORRECTION

PATENT NO. : 5,348,547
DATED : September 20, 1994
INVENTOR(S) : Michael Payne, et al It is certified that error appears in the above-indentified patent and that said Letters Patent is hereby corrected as shown below:

*Column 15, line 56, "diminishino" should read --diminishing--.*

*Column 18, line 35, "introductiont" should read --introduction.--.*
*Column 19, line 2, "uncutling" should read --uncurling--.*
*Column 19, line 8, "structsre" should read --structure--.*
*Column 19, line 22, "uncutling" should read --uncurling--*
*Column 20, line 47, "59" should read --58--.*
*Column 21, line 58, "with" should read --will--.*
*Column 21, line 60 "g" after "0.09" should be omitted.*
*Column 22, line 11, "weiqht" should read --weight--.*
*Column 22, line 18, "reDion" should read --region--.*
*Column 26, line 61, "mole" should read --more--.*
*Column 27, line 5, "ho)d" should read --hold--.*
*Column 29, line 12, "positioend" should read --positioned--.*
*Column 29, line 14, "havinq" should read --having--.*
*Column 29, line 14, "edqe" should read --edge--.*
*Column 29, line 15, "edqe" should read --edge--.*
*Column 29, line 16, "pattially" should read --partially--.*
*Column 29, line 17, "edqes" should read --edges--.*
*Column 29, line 18, "extendinq" should read --extending--.*

UNITED STATES PATENT AND TRADEMARK OFFICE
CERTIFICATE OF CORRECTION

PATENT NO. : 5,348,547
DATED : September 20, 1994
INVENTOR(S) : Michael Payne, et al It is certified that error appears in the above-indentified patent and that said Letters Patent is hereby corrected as shown below:

Column 29, line 26, "pattially" should read --partially--.

Column 29, line 40, "introuduced" should read --introduced--.

Column 29, line 40, "siad acquisiton" should read --said acquisition--.

Column 29, line 59, "acquicition" should read --acquisition--.

Column 29, line 64, "wherien" should read --wherein--.

Column 29, line 65, "acquisiton" should read --acquisition--.

Column 30, line 12, "betwee" should read --between--.

Column 30, line 66, "compri sing" should read --comprising--.

Column 31, line 7, "hydrophil ic" should read --hydrophilic--.

Column 31, line 19, "l iquid" should read --liquid--.

Column 31, line 21, "general ly" should read --generally--.

Column 31, line 24, "leust" should read --least--

Signed and Sealed this

Twelfth Day of December, 1995

Attest:

BRUCE LEHMAN

Attesting Officer

Commissioner of Patents and Trademarks